United States Patent [19]

Phipps et al.

[11] Patent Number: 5,423,739
[45] Date of Patent: Jun. 13, 1995

[54] DEVICE AND METHOD FOR IONTOPHORETIC DRUG DELIVERY

[75] Inventors: Joseph B. Phipps, Plymouth; Warren W. Howland, Champlin; Allan H. Jevne, Anoka; Carolann Holmblad, Cambridge, all of Minn.

[73] Assignee: Alza Corporation, Palo Alto, Calif.

[21] Appl. No.: 100,071

[22] Filed: Jul. 30, 1993

Related U.S. Application Data

[63] Continuation of Ser. No. 675,313, Mar. 26, 1991, abandoned, which is a continuation-in-part of Ser. No. 502,841, Mar. 30, 1990, abandoned.

[51] Int. Cl.$^6$ .............................................. A61N 1/30
[52] U.S. Cl. .................................... 604/20; 607/149; 607/152; 607/153
[58] Field of Search ............... 128/803, 802, 639, 640, 128/641; 604/20; 607/149, 152, 153

[56] References Cited

U.S. PATENT DOCUMENTS

| | | |
|---|---|---|
| 3,812,071 | 5/1974 | Stoy . |
| 3,929,741 | 12/1975 | Laskey . |
| 3,991,755 | 11/1976 | Vernon et al. . |
| 3,994,302 | 11/1976 | Brennen . |
| 3,998,215 | 12/1976 | Anderson et al. . |
| 4,021,382 | 5/1977 | Stoy et al. . |
| 4,051,842 | 10/1977 | Hazel et al. . |
| 4,066,078 | 1/1978 | Berg . |
| 4,094,822 | 6/1978 | Kater . |
| 4,140,122 | 2/1979 | Kuhl et al. . |
| 4,141,359 | 2/1979 | Jacobsen et al. . |
| 4,273,135 | 6/1981 | Larimore et al. . |
| 4,274,420 | 6/1981 | Hymes . |
| 4,352,359 | 10/1982 | Larimore et al. . |
| 4,383,529 | 5/1983 | Webster . |
| 4,391,278 | 7/1983 | Cahalan et al. . |
| 4,419,092 | 12/1983 | Jacobsen et al. . |
| 4,474,570 | 10/1984 | Ariura et al. . |
| 4,524,087 | 6/1985 | Engel . |
| 4,526,176 | 7/1985 | Bremer et al. ...................... 128/803 |
| 4,557,723 | 12/1985 | Sibalis . |
| 4,585,652 | 4/1986 | Miller et al. . |
| 4,593,053 | 6/1986 | Jevne et al. . |
| 4,601,286 | 6/1986 | Kaufman . |
| 4,622,031 | 11/1986 | Sibalis . |
| 4,645,502 | 2/1987 | Gale et al. . |
| 4,655,767 | 4/1987 | Woodard et al. . |
| 4,693,711 | 9/1987 | Bremer et al. . |
| 4,699,146 | 10/1987 | Sieverding . |
| 4,708,716 | 11/1987 | Sibalis . |

(List continued on next page.)

FOREIGN PATENT DOCUMENTS

| | | |
|---|---|---|
| 0182520 | 5/1986 | European Pat. Off. . |
| 0252732 | 1/1988 | European Pat. Off. . |
| 87/01676 | 2/1988 | European Pat. Off. . |
| 0269246 | 6/1988 | European Pat. Off. . |
| 0299615 | 1/1989 | European Pat. Off. . |
| 0318776 | 6/1989 | European Pat. Off. . |
| 0337642 | 10/1989 | European Pat. Off. . |
| WO/8803821 | 6/1988 | WIPO . |

OTHER PUBLICATIONS

"Acetic Acid Iontophoresis for Calcium Deposits," by J. Kahn, *Physical Therapy*, 57, 658 (1977).
"Iontophoretic Delivery of Drugs: Fundamentals, Developments and Biomedical Applications," by A. K.

(List continued on next page.)

*Primary Examiner*—Krista M. Pfaffle
*Attorney, Agent, or Firm*—Merchant, Gould, Smith, Edell, Welter & Schmidt

[57] ABSTRACT

An iontophoretic device having a two-layer active electrode element is disclosed. The active element is composed of overlapping skin contact hydrogel and carrier layers. The carrier layer contains dispersed or dissolved active agent. The active electrode element maintains the active agent in stable form and permits efficient transport of the active agent to the host. Also disclosed is an iontophoretic device having a single layer active electrode element. The single layer is a hydrogel as manufactured or substantially dry and capable of being hydrated before use. The skin contact hydrogel of the two-layer active electrode element preferably.

44 Claims, 3 Drawing Sheets

U.S. PATENT DOCUMENTS

| | | |
|---|---|---|
| 4,722,726 | 2/1988 | Sanderson et al. . |
| 4,731,049 | 3/1988 | Parsi .................................... 128/803 |
| 4,734,090 | 3/1988 | Sibalis . |
| 4,744,787 | 5/1988 | Phipps et al. . |
| 4,747,819 | 5/1988 | Phipps et al. .................... 128/803 |
| 4,747,845 | 5/1988 | Korol . |
| 4,768,503 | 9/1988 | Highgate et al. . |
| 4,768,523 | 9/1988 | Cahalan et al. .................... 128/785 |
| 4,786,277 | 11/1988 | Powers et al. . |
| 4,814,168 | 3/1989 | Sablotsky et al. . |
| 4,817,594 | 4/1989 | Juhasz . |
| 4,820,263 | 4/1989 | Spevak et al. . |
| 4,842,577 | 6/1989 | Konno et al. . |
| 4,927,408 | 5/1990 | Haak et al. ............................ 604/20 |
| 5,057,072 | 10/1991 | Phipps .................................... 604/20 |
| 5,084,006 | 1/1992 | Lew et al. ............................. 604/20 |
| 5,084,008 | 1/1992 | Phipps .................................... 604/20 |

OTHER PUBLICATIONS

Banga et al., *Journal of Controlled Release*, 7, 1–24 (1988).

"Transport of Ionic Species Through Skin," by J. B. Phipps et al., *Solid State Ionics*, 28–30, 1778–1783 (1988).

"Iontophoretic Delivery of Model Inorganic and Drug Ions," by J. B. Phipps et al., *Journal of Pharmaceutical Sciences*, 78, 365–369 (1989).

"The Effect of Extraneous Ions on the Transdermal Iontophoretic Delivery of Hydromorphone," J. B. Phipps et al., *Abstract from the Controlled Release Society Meeting*, (Aug., 1989).

"Noninvasive Delivery of a Novel Inotropic Catecholamine: Iontophoretic Versus Intravenous Infusion in Dogs," by J. E. Sanderson et al., *Journal of Pharmaceutical Sciences*, 76, 215–218 (1987).

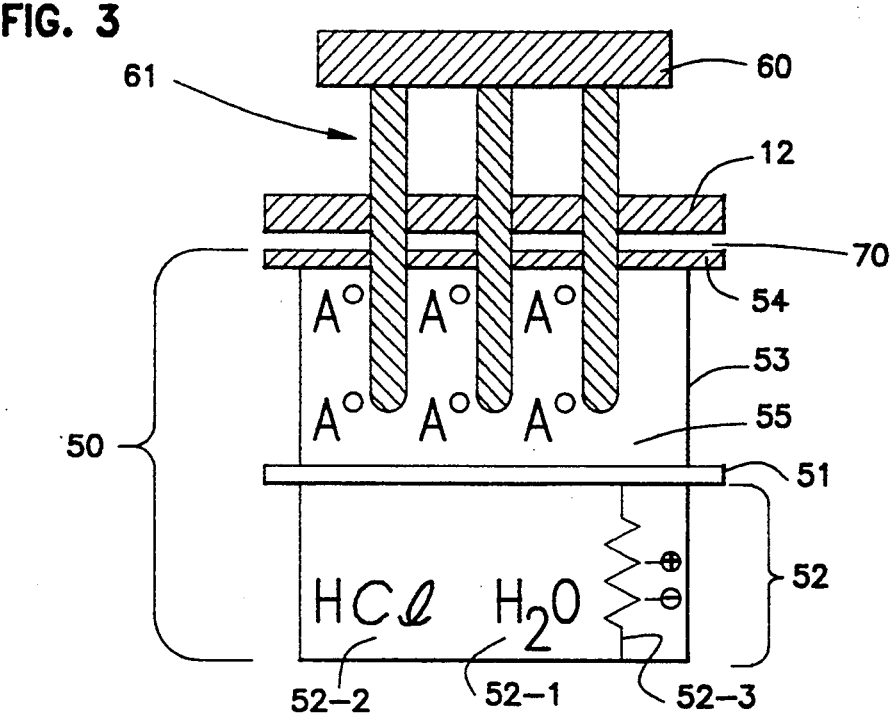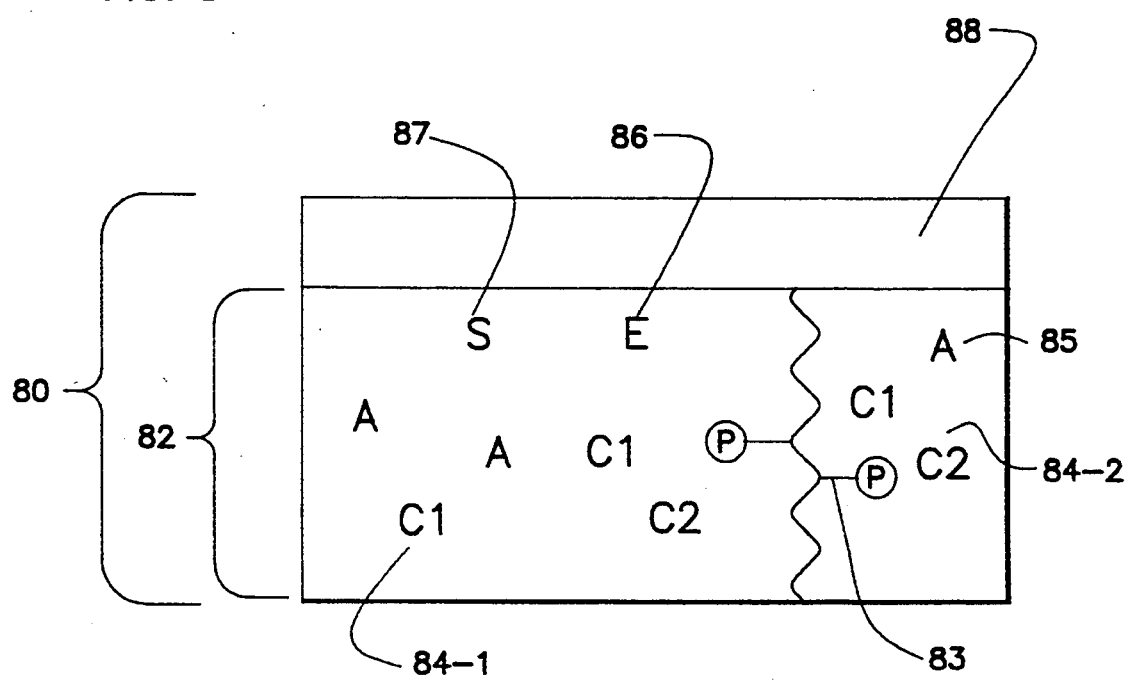

1. Polymer$^{\oplus}$ $Cl^{\ominus}$ /Polymer$^0$ $^{\oplus}$ H → Polymer$^{\oplus}$ /Polymer$^0$ + HCl 2. A$^0$ + H$^{\oplus}$ → AH$^+$ 3. Cl$^{\ominus}$ + Ag → AgCl + e$^{\ominus}$

DEVICE AND METHOD FOR IONTOPHORETIC DRUG DELIVERY

CROSS-REFERENCE TO RELATED APPLICATION

This is a continuation of application Ser. No. 07/675313, filed Mar. 26, 1991, now abandoned, which is a continuation-in-part of U.S. patent application Ser. No. 07/502,841, filed Mar. 30, 1990, now abandoned.

FIELD OF THE INVENTION

This invention relates to an iontophoretic active element of hydrogel and an active agent.

DESCRIPTION OF THE PRIOR ART

Iontophoresis is a method for introducing active agents into a host. The method utilizes direct electrical current to transport the active agents, which are usually in charged form, through the skin, mucosa or other body surface of the host. This method has proven to be very useful in numerous medical applications. U.S. Pat. Nos. 3,991,755 and 4,141,359 for example, disclose iontophoretic devices and their applications. The iontophoretic process has been found to be useful in the administration of lidocaine hydrochloride, hydrocortisone derivatives, penicillin, dexamethasone sodium phosphate and many other pharmaceutical agents. Iontophoretic methods have also been employed to deliver uncharged therapeutic agents by the mechanism of induced solvent flow.

Iontophoretic devices employ two electrode means for accomplishing this method. The first electrode means, called the active electrode, is the element from which the active agent is transported into the body. The second electrode means, called the counter or ground electrode, serves to close the electrical circuit through the body. In typical applications the active electrode holds, contains or otherwise has available to it a source of the active agent. Thus, the active electrode is usually complex compared to the counter electrode.

U.S. Pat. No. 3,991,755 discloses several examples of active electrodes. In one example, the electrode is a stainless steel wire housed in a plastic sheath which is shaped to safely fit within the ear canal. A liquid solution containing the active agent is poured into the ear and held in place by the sheath with wire contact. In another example, the electrode wire in a plastic sheath, having an opening, houses a wad of absorbent material holding a liquid containing the active agent. The sheath and wad are taped to the skin.

U.S. Pat. No. 4,141,359 discloses several variations of an active electrode containing a conductive gel. All of the embodiments include a receptacle for holding either a conducting gel in which the active agent is dissolved, or for holding a sponge which is saturated with the conductive gel and the active agent. The conducting gel/active agent solution communicates with the body tissue through a hole in the receptacle. The receptacle is held in contact with the skin by an adhesive pad surrounding the receptacle or a strap attached to the pad. In other embodiments, the hole in the receptacle is covered with a membrane and the ionic substance is driven through the membrane by the electric current.

In "Acetic Acid Iontophoresis for Calcium Deposits", *Physical Therapy*, Vol. 57, No. 6, June, 1977 (pp. 658-659), Joseph Kahn discloses an active electrode formed by a gauze pad soaked in the solution containing active agent. The pad is overlaid by several layers of paper towels moistened with water. A section of block tin or aluminum foil is placed over the moistened towel and connected to the iontophoretic current generator by means of a wire and alligator clip.

U.S. Pat. No. 4,820,263 discloses a combination of an adhesive material and active agent for use as the active electrode. The adhesive material is a nonionic, polymeric material that is or can be made tacky and can dissolve or disperse pharmaceutical agents.

The active electrodes of the prior art have a number of disadvantages. Those in which the active agent is held in solution in a liquid are relatively messy. When the liquid is not contained in an absorbent material, the electrodes are used in situations where body cavities form a natural container for the liquid, or a cup or other container is employed to hold the liquid on the body surface. The electrodes employing a conductive gel in which the active agent is dissolved are somewhat less messy, but still leave a residue of gel after use. The electrodes employing the membrane alleviate the gel residue but create additional complexities in the construction and handling of the electrode and active agent.

Electrodes constructed of an adhesive gel adhere readily to the skin but many polymeric substances needed to develop adhesiveness are not compatible with charged pharmaceutical agents. In typical applications, the polymer and agent may separate or the pharmaceutical agent may not be released in sufficient quantity. Attempts to circumvent the incompatibility by substitution of ionic groups onto the polymer can result in diminished transfer of active agent into the host if a strong interaction between the agent and polymer results or if competing ions (i.e., ions with the same charge as the therapeutic ion) are present in excessive quantity.

These disadvantages all result in an inability to precisely control administration of the active agent and/or result in an energy inefficient device due to the large current required to transport the active agent. Control is nevertheless needed to sustain a therapeutical blood level of the agent being administered. Many active electrodes of the prior art require complex procedures for handling the material containing the active agent prior to and, in some electrodes, during the iontophoretic process. A simpler electrode would permit the iontophoretic process to be much more widely applied, not only in known applications but also in many new applications that previously were not practical. A further disadvantage is the short shelf life of the electrodes especially those constructed of hydrogels. Inventory cannot be maintained over the long term because the aqueous medium often causes decomposition of the active agent.

Therefore, it is an object of the invention to develop an active electrode element that is compatible with active agents such as pharmaceuticals and chemicals and preferably adhesive. A further object is the development of an active electrode element that is capable of minimizing degradation of active agent when the electrode means is in storage. Yet another object is the development of an active electrode element that will efficiently transport to the skin or mucosa the active agent.

SUMMARY OF THE INVENTION

The invention is directed to an active electrode element, an iontophoretic device containing the active element and a method of administering an active agent through use of the iontophoretic device.

The iontophoretic device includes a housing that preferably is insulated, a source of current and current control preferably mounted within the housing, a counter electrode element in electrical contact with one pole of the current source and an active electrode element in electrical contact with the other pole of the current source preferably through an electrode plate means (e.g., foil, mesh, metallic particles, and the like).

The first configuration of the active electrode element is a single layer arrangement containing an ionic polymer component optionally in combination with other neutral polymer components. The ionic polymer is cationic, anionic or preferably amphoteric and may be from about 1% to about 100% by weight of the total polymer or polymers present. The polymer layer may be in the form of a hydrogel or substantially dry. When substantially dry, the polymer layer is formulated to be suitable for conversion to a hydrogel having the electrochemical, drug delivery and adhesive properties desired for the element. The polymer layer has an appropriate pH and other properties for maintaining the active agent without decomposition. The ionic polymer component of the polymer layer has the same charge as the ionized active agent. When the ionic polymer is amphoteric, both the ionized active agent and other ions act as mobile counter ions for the amphoteric polymer. The charge of substantially all of these "other ions" is opposite the charge of the ionized active agent.

When the active agent is stable in a hydrogel formulation, the single layer element can be produced directly in the hydrogel form. In this case, the active agent is preferably incorporated into the hydrogel during element manufacture.

When the polymer layer is substantially dry, the single layer element is constructed so that the conversion to hydrogel can be accomplished by a hydration process such as injection or soaking with or otherwise contacting an aqueous medium. The substantially dry single layer element can be formed with or without active agent. If the active agent is not present, it can be added during the hydration process shortly before use. In a preferred embodiment, the element contains dry amphoteric polymer having an appropriate pH for active agent stability, and containing the active agent. The element is hydrated by its contact with an aqueous medium so that the transport and optional adhesive properties are developed. The element is preferably designed to be electrochemically appropriate for transport of active agent by maintaining an insignificant quantity of competing ions during operation.

The second configuration of the active electrode element is a two layer arrangement with the layers, when allowed to interact, being capable of conducting current when operated iontophoretically. The first or skin contact layer is a hydrogel composed of ionic organic polymers, optional neutral polymers and ionic excipients for converting the neutral active agent to an ionic form, if appropriate. The second or carrier layer contains dissolved or dispersed active agent. The carrier layer may be an organic polymer or natural or semi-synthetic material and preferably has few or no mobile ionizable substances other than the active agent.

The form of the matrix may be a powder, unitary solid, gel, hydrogel, liquid or viscous fluid. Preferably, the carrier layer is a hydratable organic polymer matrix.

The two layers of the second configuration of the active element are constructed so that immediately upon their contact the active agent is released from the carrier layer to the skin contact layer. The release can occur during manufacture of the element or later by the intentional act of the user. In a preferred embodiment, the element is an insert that can be fitted onto the electrode plate within an active electrode compartment of an iontophoretic device. Alternatively, the two layer element can be permanently mounted on the electrode plate.

In one embodiment of the two layer element and as a feature of the single layer formulation, the mobile counter ions of the hydrogel have a charge opposite from that of the ionized active agent. If the ionized active agent is a cation, the hydrogel polymer is cationic, e.g., a polymeric quaternary ammonium salt, and its mobile counter-ion is anionic, e.g., chloride. If the ionized active agent is an anion, the foregoing hydrogel polymer charge distribution is reversed, e.g., a polyacrylate and hydronium. If the hydrogel polymer is amphoteric substantially all mobile counter ions have a charge opposite from that of the ionized active agent.

A preferred embodiment of the two layer active electrode element includes an impermeable barrier between the two layers. The carrier layer is optionally designed to contain little or no water and to maintain about a preferred pH so that decomposition of the active agent over a long term is minimized. Breaching the impermeable barrier results in migration of the active agent from carrier layer to the skin contact layer. If the carrier layer is a solid gel, powder, hydrogel or other shape retaining material the barrier can be a film between the two layers. If the carrier layer is fluid, semi-fluid or viscous, the barrier can be a containing means such as a pouch, bag or a combination of the walls of the element housing and a covering film or membrane.

A preferred embodiment of the active electrode element with impermeable barrier concerns a carrier layer dispersion of the active agent in neutral form. In this embodiment, the skin contact layer contains the appropriate reagent for converting the active agent to an ionic form. Breaching the impermeable barrier during use initiates the conversion. Incorporation of higher concentrations and stability of the active agent in the active element are increased by this embodiment.

A further preferred embodiment of the active electrode element concerns the use of an amphoteric polymer component in the skin contact layer of the two layer element and as a polymer component of the single layer element. The two layer element optionally includes a hydrogel skin contact layer with acid or base in an amount sufficient to ionize the active agent, an impermeable barrier, a carrier layer containing an active agent in neutral form but that is capable of forming a charged form by reaction with hydronium or hydroxyl ion, and an electrode plate of a composition that will interact with the non-active agent, mobile counter-ion during operation to form a substantially neutral, insoluble or immobile substance. In the single layer element, when the polymer is substantially dry, an aqueous medium optionally containing ionized active agent, ionized active agent or ionizing reagent (acid or base) may be added to form the active agent loaded hydrogel. The dry polymer will respectively contain ionizing reagent, polymer alone or active agent in unionized form. The single layer element also includes an electrode plate of a composition that will interact with mobile counter-ion during operation to form a substantial neutral, immobile, or insoluble substance.

The method of the invention is directed to administration of the active agent to a host by the application of an electric potential which results in the transport of the agent through the skin or mucosa of the host. The method includes the steps of applying the foregoing iontophoretic device in activated form to the skin or mucosa of the host to be treated and generating an electric potential between the active electrode element and the skin or mucosa.

BRIEF DESCRIPTION OF THE DRAWINGS

FIG. 3 is a sectional view of an embodiment of the active electrode element according to the invention;

DETAILED DESCRIPTION OF THE INVENTION

Figure 1:
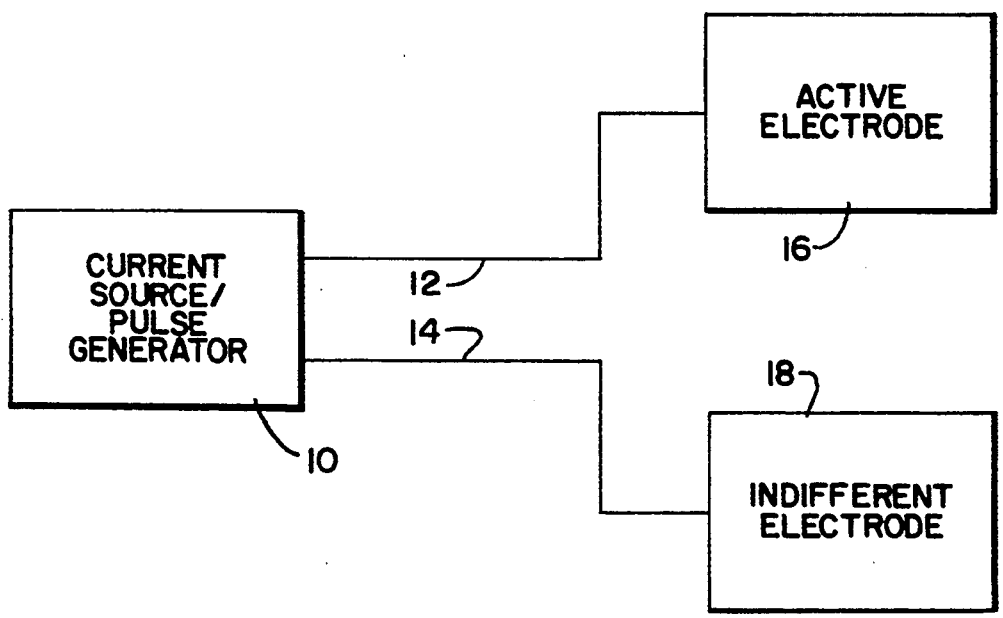
FIG. 1 is a diagrammatic illustration showing an iontophoretic system employing active and counter electrode elements.

The invention provides an active electrode element for use in the iontophoretic introduction of an active agent into a host. The electrode element is composed of a single layer with at least one ionic polymer component and optional active agent, or is composed of two layers; the skin contact layer being a hydrogel and preferably adhesive and the carrier layer containing the active agent. In the single layer configuration, the polymer may be in a hydrogel form or substantially dry. When it is substantially dry, the polymer will be hydrated to hydrogel form shortly before use. In the two layer configuration, the active agent of the second carrier layer is preferably permitted to move into the first layer shortly before use although the combination of the active agent into the first layer can occur upon manufacture if the active agent displays aqueous stability. In use, the active element is combined with a means for electrically transporting the active agent through the skin or mucosa of the host.

Preferably, the single layer element or the skin contact layer of the two layer element, is partially or entirely composed of an organic polymer with ionizable groups such that this ionic organic polymer component is cationic, anionic or amphoteric (zwitter-ionic). Non-ionic, neutral polymers can be added to the polymer composition of the element to provide a desirable stoichiometric balance between the active agent ions and the cationic and/or the anionic groups of the ionizable organic polymer component. In its final form for use the single layer is a hydrogel. When fabricated in a substantially dry state the single layer is hydratable to a hydrogel. The ionic organic polymer component may be chosen so that its charge is the same as the ionized active agent. The charge of any non-active mobile counter-ion is preferably opposite that of the ionized active agent.

Preferably, the carrier layer of the two layer element is composed of an organic polymer matrix containing polar groups such as alcohol, amide, ketone, heterocycle or ester. Other ingredients may be included in both layers so long as they do not adversely affect the iontophoretic process, active agent compatibility within the carrier layer and matrix quality of the skin contact layer.

The ionic polymer component of the hydrogel single layer element or the skin contact hydrogel layer of the two layer element may be prepared from any organic monomer carrying pendent ionizable groups by various polymerization techniques with monomer intermolecular coupling and/or light to medium cross-linking using a difunctional or multi-functional cross-linking reagent to form a gel product. Preferably, when this polymer is hydrated to a hydrogel, it exhibits tackiness or adhesiveness and contains a large portion of water such as about 10 to 99% percent by weight. If the hydrogel is not sufficiently adhesive to hold the iontophoretic device to the patient, then a peripheral adhesive can be employed. Examples of such hydrogels include gelled and/or cross-linked water swellable polyolefins, polycarbonates, polyesters, polyamides, polyethers, polyepoxides and polyurethanes carrying such pendent substituents as (alkyl, aryl or aralkyl) carboxylic, phosphoric, glycolic or sulfonic acids, (alkyl, aryl or aralkyl) quaternary ammonium salts and protonated amines and/or other positively charged species. Combinations of individual polymers to form the adhesive hydrogel also can be used. Preferred formulations include gel polymers of ethylenically unsaturated carboxylic or sulfonic acid such as polyacrylic acids, poly(acrylamido alkyl or aryl carboxylic or sulfonic acid), poly[N-(tetramethyl aminoethyl) acrylamide] chloride and poly(acrylamido alkyl or aryl phosphoric or glycolic acid). Further detail and discussion of the hydrogel formation techniques, the gelation and cross-linking processes and modifications to develop adhesiveness and/or tackiness may be found in "Handbook of Adhesives," I. Skeist Ed., Van Norstrand Reinhold & Co., N.Y. 1977, the disclosure of which is incorporated herein by reference. Additives for increased tackiness, plasticity, pH control, antisepsis, antioxidation, bacterial control, syneresis, fungal control and the like can be combined with the hydrogel during polymerization or blended during later optional water swelling. An especially preferred embodiment is an amphoteric hydrogel which will contain both acid pendent groups (e.g., sulfonic) and basic pendent groups (e.g., amino or quaternary ammonium pendent groups). It can be formed by combining a sulfonic or carboxylic acid hydrogel polymer with an amine hydrogel polymer and shearing or extruding to homogenize the mixture. Alternatively, the amphoteric hydrogel can be produced as a copolymer by copolymerization of the corresponding monomers.

The substantially dry single layer element incorporating the foregoing polymers in a dehydrated state can be formed by polymerization of monomers or by formulation from preformed polymers either in a hydrated or an unhydrated state as described above. Any of these forms may optionally contain the active agent. If the single layer polymeric element is first formed as a hydrogel, it can be partially or wholly dehydrated under mild conditions, such as vacuum evaporation, sublimation, desiccation and the like to remove loosely and tightly bound water of hydration. If the single layer element is formed from unhydrated but polymerized material or by polymerizing monomer to form the unhydrated material, it can be formed directly into the dehydrated layer. The active agent can be optionally incorporated into any of these forms.

In its simplest embodiment, the carrier layer of the two layer configuration may simply consist of the drug in a solid or powdered form. The carrier layer can be a matrix holding the dispersed or dissolved active agent but permitting its immediate release to the skin contact layer when the two layers of the active element contact each other or when the active element is activated as described below. The matrix can have any physical form capable of performing the foregoing functions. Gels, hydrogels, slurries, semi-fluid or viscous mixtures, powders, liquids and solid immediate release structures are included. When the carrier layer is fluid, slurry, powder, semi-fluid or viscous, it can be held by a containing means. The containing means acts as the barrier which, when breached, will permit immediate contact between the carrier and skin contact layers. When the carrier layer is a solid, gel or hydrogel, it will be self-shape retaining.

If an organic polymer is used in the carrier layer of the two layer element, it may be prepared from any organic monomer carrying pendent ionic or nonionic groups, by aqueous or organic emulsion or solution polymerization to form a gel product that swells when contacted by water. The carrier layer may also be any natural or semisynthetic polar material that possesses the foregoing functions. Combinations of individual polymers and/or materials can also be used in the hydrogel. Examples include single or multiple combinations of inorganic materials such as talc, soapstone, silicones and organic polymers such as polyolefins, polycarbohydrates such as dextrans, starches, alginates, polycarbonates, polyesters, polyamides, polyethers, polyepoxides and polyurethanes carrying such pendent substituents as (alkyl, aryl or aralkyl) alcohol, (alkyl, aryl or aralkyl) amide, (alkyl, aryl or aralkyl) nitrogen heterocyclic groups such as pyrrolidone or pyridine, alkyl groups. Preferred organic polymers include polyvinyl alcohol, and/or polyvinyl pyrrolidone. Examples of natural or semi-synthetic organic materials include cellulosic derivatives, alginate derivatives, starch derivatives, dextrans, collagen and microbial polysaccharides. Further detail and discussion of the carrier layer polymer preparation techniques may be found in "Polymer Science and Materials", A. Tobolsky and H. Mark Ed., Wiley Interscience, Princeton, N.J. 1971, the disclosure of which is incorporated herein by reference.

The carrier layer is formulated to be compatible with the active agent and to readily release active agent to the skin contacting layer. Additives for plasticity, pH control, antisepsis, antioxidation, bacterial control, syneresis and fungal control and the like can also be combined into the carrier layer.

In the preferred embodiments where the carrier layer contains little or no water, the dry ingredients are mixed together or added to a semi-fluid mixture one at a time. If the active agent is also dry it can be included here. Otherwise, the carrier layer ingredients are combined in aqueous medium to form a mixture. The mixture can be kneaded, extruded, mixed, blended, sheared and/or stirred until a substantially homogenous material results. When the carrier layer is to be a solid, gel or hydrogel, allowing that material to be quiescent will cause resolidification. When the carrier layer is to be a powder, the homogenation will produce a substantially uniform distribution of active agent absorbed on or within the powdered polymer or natural or semisynthetic material. When the carrier layer is a liquid, semifluid or viscous material, combining the ingredients together by mixing, spraying and the like forms the layer.

The impermeable barrier of a preferred embodiment of the active electrode two layer element may be constructed of any organic or inorganic material that is impervious to water; acid or base. Examples include nonpolar polyolefins such as polypropylene, polyester, polyethylene, polyvinyl chloride, polystyrene and polycarbonate and metallized laminates thereof. When the barrier is a film, to allow release of the film from the hydrogel layers, the film surface may be coated with a release coating agent such as silicone.

To construct the single layer element and the skin contact layer of the two layer electrode element, the appropriate polymer composition can be appropriately shaped by extrusion of the preformed polymer and optional other ingredients into a mold or directly into the iontophoretic housing. Alternatively, the monomeric mixture can be polymerized, gelled and/or cross-linked directly within the mold or housing with addition of optional other ingredients at appropriate intervals during the polymerization. The formed skin contact layer is allowed to cure to a shape retaining form.

To construct the carrier layer of the two layer element, a free-flowing mixture of carrier layer polymer and/or natural or semi-synthetic material, as well as active agent and optional other ingredients is introduced as a covering layer over the cured skin contact layer and allowed to resolidify to a solid form. When the carrier layer is a liquid or semi-fluid or viscous material it is first introduced into the container means and then positioned on top of the skin contact layer.

In the case of a permanently mounted active electrode element, the single layer or the skin contact layer is formed in situ within the iontophoretic housing by the foregoing process. For the two layer element, the skin contact layer may be formed before or after formation of the carrier layer within the housing. If formed before, the housing may be of two joinable parts, the first being for the skin contact layer and the second for the carrier layer. In the case of an insert, the single or two layer element is formed in a mold, removed after formation and packaged for storage. When the two layer element containing the impervious barrier is constructed, the barrier is positioned onto the surface of the cured adhesive hydrogel before introducing the carrier layer with active agent or the barrier may be pre-positioned so as to segregate the carrier layer with active agent from a subsequent in situ prepared hydrogel.

The invention can adopt a wide variety of embodiments. In one embodiment the active electrode element can be a plug of the single layer or two layer element in any suitable size and shape formed by the molding technique described above. The plug may be applied to the body and may be connected to an iontophoretic generator by a wire or other electrically conductive means. The carrier layer of the two layer plug serves as a solid or liquid reservoir for the active agent, as the means for holding the electrode element to the body, and the means for conducting the active agent into the body. The polymer of the single layer electrode serves all of these functions. Alternatively, the single or two layer plug may be an insert of a size and shape suitable for application to an electrode plate of an iontophoretic current generator.

Depending upon the structural features present, various advantages arise from the embodiments incorporating the active agent into the single layer element or into the two layer element. Electrodes for iontophoretic devices can be made much simpler since the active electrode element may serve as its own reservoir of active agent. Receptacle structures such as cups, absorbent swabs, membranes and the like may be eliminated. The active element also serves as a means for attaching the electrode to the body, and thus the straps, adhesive attachments pads and the like can be eliminated. The invention also provides for precise delivery of dosage of the active agent, since the layer or layers are composed of strong structural materials that cannot easily become separated. The entire surface of the element is held firmly to the body, even under the condition of considerable movement of the body. This adherence serves to facilitate precise delivery, and facilitates uniform dosage control over the body portion to which the electrode element is applied. The combination of a polymer and active agent (single layer element) and the combination of the skin contact layer for forming an intimate contact with the skin or mucosa and the carrier layer that is compatible with the active agent (two layer element) are also advantageous. The agent can be dispersed or dissolved, alternatively in neutral form, or in salt or ionic form if stable, and in high concentration in the carrier layer of the two layer element or in the polymer of the single layer or in the hydrating medium for the single layer. Upon combination, the rate of transport can be controlled by the current so as to provide a sustained therapeutic level of the active agent.

Relative to known hydrogel elements these combinations display a better ability to stabilize and to transport the active agent to the patient in an efficient manner. The dry single layer element and the two layer element of the invention, in particular, lessen the chance of active agent decomposition for those active agents that have non-aqueous stability. Appropriate pH and water content can be maintained in the substantially dry polymer layer of the single layer element or in the carrier layer of the two layer element so as to avoid the sometimes deleterious effects of high or low pH and water. Decomposition of the active agent is avoided by first forming the hydrogel and then adding the active agent. This advantage is gained by the method for use of the substantially dry single layer element and the two layer element.

For the substantially dry single layer element, the invention may be practiced by first hydrating the element with a supplied aqueous or alcohol/aqueous medium. The medium is dripped, soaked, injected, coated or otherwise applied to the element. Although the active agent preferably is already present within the single layer element, it can alternatively be added as an ingredient in the hydrating medium. The hydrogel layers of the single layer elements whether manufactured as such or derived from the substantially dry element, possess essentially the same iontophoretic properties.

The application of the single and two layer elements to the patient then follows the same course. The element containing the active agent is applied to the skin or mucosa of the host and then an electric current is generated through the element and into the skin or mucosa thereby introducing the active agent into the host. The invention may be practiced by employing the active electrode element according to the invention with a combination iontophoretic/electrical pulse stimulator. The invention contemplates that the active electrode element may be used in an iontophoretic generator that also includes an electrical nerve stimulator, an electrical muscle stimulator or a combination of both types of stimulation.

In one embodiment of the two layer active element, contact between the two layers is established upon manufacture of the element. In effect, this element is like a single layer configuration. Immediate migration of the active agent to the skin contact layer occurs when this contact is made. In another embodiment, contact between the layers is prevented by the impervious barrier between them. Contact is made by intentionally activating the element. Breaching the barrier by removal or puncture exposes the carrier layer to fluid ingredients in the skin contact layer and results in migration. If ionizing reagent is present, neutral active agent is converted to an ionized form by reaction with the ionizing reagent. The ionized active agent is transported by electric potential through the element and into the skin or mucosa.

Preferred Embodiments

The invention lends itself to iontophoretic electrodes of varying types, shapes and configurations. For exemplary purposes herein, an iontophoretic system is illustrated in diagrammatic form in FIG. 1. The system includes current source 10 which is electrically coupled through leads 12 and 14 to electrodes 16 and 18 respectively. For purposes of illustration, electrode 16 is labeled the "active" electrode while electrode 18 is labeled the "counter" electrode, although the positions may be reversed. Leads 12 and 14 may be wires or they may be any other means for electrically coupling the current source 10 and the electrodes 16 and 18.

Figure 2:
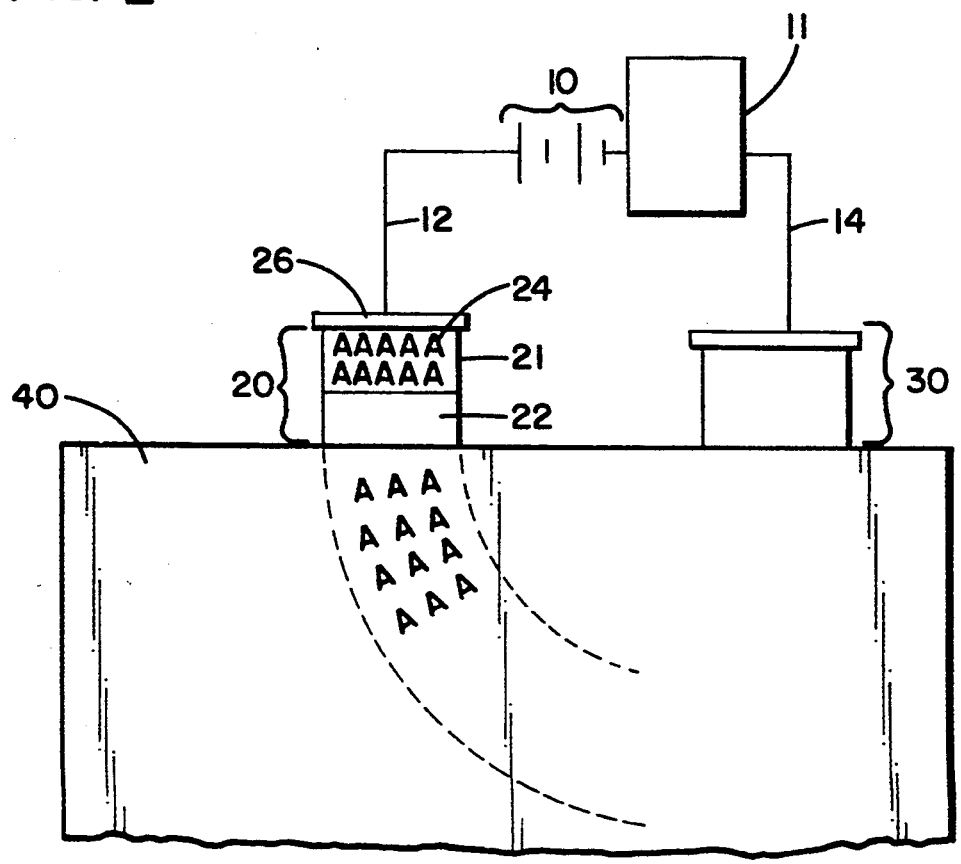
FIG. 2 is a sectional diagrammatic view of a pair of electrode elements applied to the body, illustrating the iontophoretic process.

FIG. 2 shows a sectional view of a pair of electrodes 20 and 30 which are placed upon host 40 to illustrate the iontophoretic process. Electrode 20 is the active electrode element composed of a combination of a first skin contact layer 22 and a second carrier layer 21 containing the active agent 24 and an electrode plate 26. Electrode plate 26 is shown as a plate in contact with carrier layer 21, however, the electrical connection to the current source can have any appropriate form (e.g., mesh, foil, powder) and can contact the active electrode element at any position so long as electrical conduction is afforded and that direct contact of the electrical connection plate 26 with the skin is avoided.

The ionized or ionizable active agent in carrier layer 21 is the pharmaceutical or other chemical which is to be introduced into the host. Electrode 30 is a counter electrode for completing the electric circuit through the skin of the host 40. Electrodes 20 and 30 may be coupled to a current source, such as 10, through leads, such as 12 and 14. The current source 10 may also be regulated through optional control circuit 11 which may generate electrical pulses and may be of a type suitable for either nerve or muscle stimulation. The leads 12 and 14 may be attached to electrode elements 20 and 30 in any conventional manner. When a current is generated by a current source, such as 10, and applied to electrode elements 20 and 30 in place upon host 40, a current will flow through host 40. The current will cause the ionized active agent 24 to be transported out of electrode element 20 into host 40. It should be understood that the term "host" is used in its most general sense, and can include plant, animal and human hosts.

FIG. 3 is a sectional view of an alternative preferred embodiment of the active electrode element 50 according to the invention. In this embodiment, impervious membrane sheet 51 is affixed between skin contact layer 52 and the second carrier layer 53 containing neutral active agent (A) 55. A plunger 60 with piercing elements 61 is positioned above sheet 51 and within carrier layer 53 so as to be capable of perforating sheet 51. Piercing elements 61 also protrude through backing sheet 54 and silver electrode plate 70 which is connected to the current source (not shown) through lead 12. Backing sheet 54 may be made of cloth, paper, polymer, fiber or any other similar material. In some embodiments, it may be desirable to use a conductive material as a backing sheet, as for example when the backing sheet is overlaid with an electrode plate 70 as shown. In other embodiments the electrode plate (not shown) may be inserted between backing sheet 54 and carrier layer 53 or between impervious membrane 51 and skin contact layer 52. The skin contact layer 52 contains water (52-1), ionizing reagent and chloride ion (52-2). Preferably the hydrogel is amphoteric (52-3).

Operation of the active electrode shown in FIG. 3 is accomplished by piercing membrane 51 by pushing on plunger 60. Water 52-2 in hydrogel layer 52 begins to diffuse through the perforations made by elements 61 and into carrier layer 53 where the dehydrated hydrogel present swells by hydration. Current from the current source (not shown) is switched on and electromotive transport begins. Alternatively, solvent from carrier layer 53 can diffuse through the perforations and transport agent 55 into skin contact layer 52.

Figure 4:
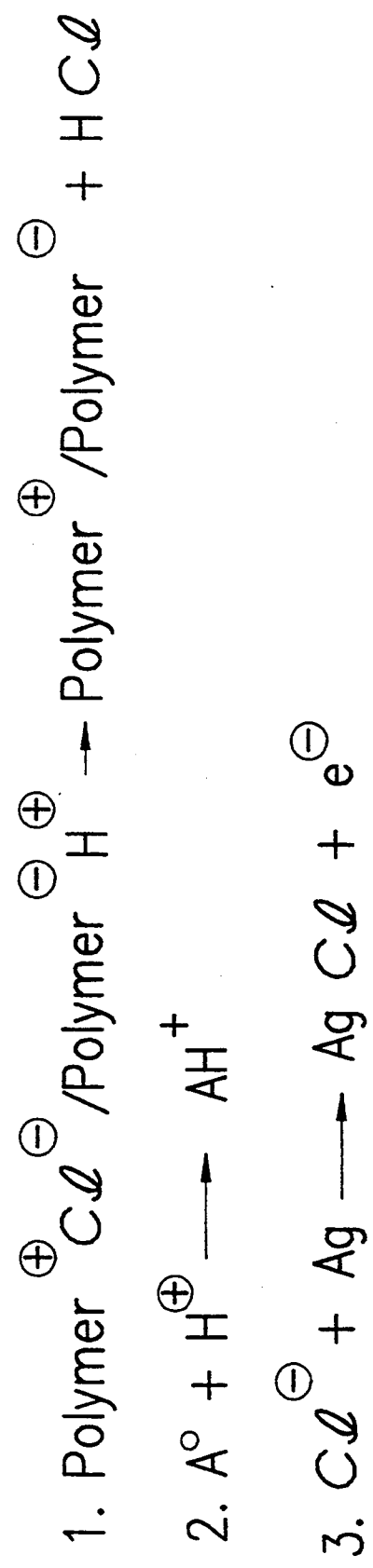
FIG. 4 is a reaction sequence for a preferred embodiment of the active electrode element of the invention; and, FIG. 5 is a diagrammatic illustration showing an iontophoretic system made of a single layer element.

The various reactions involved in the electromotive transport during operation of the two layer electrode of FIG. 3 and the single layer electrode of FIG. 5 are shown in FIG. 4. A portion of hydrogen chloride from the amphoteric polymer reacts with the active agent of the carrier layer to form $AH^+$ for electromotive transport (reactions 1 and 2) to the host. Silver plate 70 is oxidized and reacts with the chloride to form insoluble silver chloride (reaction 3). Other combinations of electrode 70 and reacting anion such as chloride, which will form insoluble inorganic or organic salts, can also be used.

FIG. 5 is a sectional view of a preferred embodiment of the single layer active electrode element 80 according to the invention. In this embodiment, the hydrogel layer 82 (manufactured as a hydrogel or derived from hydration of substantially dry polymer) contains active agent (A) 85. Active agent 85 will have a cationic or anionic form. The ionic polymer component 83 has charged pendent groups (P) of the same charge as active agent 85. The mobile counter ions C1 and C2 (84-1 and 84-2) of the active agent and the ionic polymer component respectively have an ionic charge opposite that of active agent 85. During iontophoretic operation, electrochemically generated ion E(86) interacts with one or both of the counter ions to form a substantially neutral, insoluble or immobile substance S(87). Electrode plate 88 is composed of a material which generates E (86) during operation.

When A is cationic, e.g., protonated hydromorphone, then the ionic organic polymer component is also cationic, e.g., MAPTAC, the counter ions C1 and C2 are chloride, the electrode plate 88 is silver, E(86) is silver ion and S(87) is silver chloride.

When A is anionic, e.g., salicylate, then the polymer is also anionic, e.g., AMPS, the counter ions C1 and C2 are hydronium ion, the electrode plate 88 is stainless steel, E(86) is hydroxyl ion and S(87) is water.

In each of the foregoing examples, the polymer can also be amphoteric, e.g., copolymerized MAPTAC and AMPS, provided that substantially all mobile counter ions of the amphoteric polymer C2 are either ionized active agent or other ions that are oppositely charged relative to the ionized active agent.

The advantages of this embodiment of the invention include the minimization of decomposition of active agent within the carrier layer, maintenance of charge balance within the electrode element, transport of almost all active agent to the host and long shelf storage life. In particular the dehydrated, neutral pH nature of the carrier layer facilitates the long storage life and lack of active agent decomposition.

In the embodiments shown, electrode elements 20, 50 and 80 are the active electrodes and the active agents 24, 55 and 85 are ultimately positively charged and constitute the pharmaceutical or chemical which is introduced into the body. In these embodiments, negative electrode 30 is the counter electrode. In other embodiments, it is desirable to transport a negatively charged active agent into the body, in which case the negative electrode would be active and the polarities and charges of the ionic organic polymer component of the skin contact layer, ionizing reagent and the like described above would be reversed. Embodiments for transport of both positive and negatively charged active agents which are contained in separate elements are also possible. In this case, both electrode elements will contain active agent. Embodiments for sequential administration of two similarly charged active agents which are contained in separate elements are also possible. In this case, the polarity of the electrode elements is reversible. The active agent may also be a combination of substances which are to be introduced into the body. In some instances since it may be desired to introduce more than one active agent of the same charge into the body and thus several active agents may be included in the same active electrode element.

The composition of the active electrode elements of the invention may include ingredients to control or alter the physical properties of the element. Surfactants may be added to the carrier layer to control the active agent release rate and matrix density. Humectants and water may be added the carrier to control the wetness. Preservatives may be added to extend the shelf life and/or the useful life of the product. Inert fillers may be added to control the bulk or dilute or adjust other properties. Tackifiers may be added to the skin contact layer to control tackiness. Preferably, the physical properties are adjusted so that the active electrode element is solid, that is, its consistency is such that the material does not perceptively flow. It is also contemplated that the composition may be manufactured and sold in a liquid form which upon application to the electrode plate mold or housing or backing materials changes to a solid form by drying, chemical reaction or otherwise.

Ingredients may also be added to the composition to color it. The coloring of the electrode element may be used as a code to identify the active agent which is admixed in the particular electrode or electrode element.

The hydrated hydrogel layer of the single layer element and the skin contact layer of the two layer element have an adherent property that may be augmented by one or more synthetic or naturally occurring polar, nonionic polymers, a tackifier, a humectant and water.

The polymers used for the polymer of the carrier layer contain essentially nonionic synthetic and/or naturally occurring polymeric compounds. A polar nature is preferable when the active agent is polar and/or capable of being ionic since it will assure solubility. A nonpolar nature is preferred when the active agent is neutral. The carrier layer will preferably be water swellable. Synthetic polymers suitable for use in the carrier layer of the iontophoretic electrode element are exemplified by: poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(allyl alcohol). Hydroxyl functional condensation polymers (i.e., polyesters, polycarbonates, polyurethanes) are also examples of polar synthetic polymers suitable for use in the carrier layer. Polar naturally occurring polymers (or derivatives thereof) suitable for use in the carrier layer are exemplified by: cellulose ethers, methyl cellulose ethers, cellulose and hydroxylated cellulose, methyl cellulose and hydroxylated methyl cellulose, gums such as guar, locust, karaya, xanthan gelatin, and derivatives thereof.

The "ionomeric" polymers used for the hydropolymer layer of the single layer element and the skin contact layer of the two layer element include poly(acrylic acids), poly(acrylic sulfonic acids), poly(acrylic phosphoric acids) and poly(acrylic glycolic acids), polyvinyl amines, polymers with pendent amine groups including aromatic amine groups optionally in combination with tackifiers which may be included in the adhesive composition. Tackifiers are exemplified by the following materials: polybutene, terpene resins, rosin resins, paraffinic oils, glycols, glycerine, and sorbitol. Humectants which may be included are exemplified by: glycols, glycerine and sorbitol.

Active agents useful in the present invention include any pharmaceutical compound or chemical that is capable of being ionized or converted to a charged form and would be administered to a host including animals and man for the purpose of obtaining a therapeutic effect. A variety of active agents intended to be introduced into the host may be combined with the carrier layer. In general, this includes therapeutic agents in all of the major therapeutic areas including, but not limited to, anti-infectives such as antibiotics and antiviral agents, analgesics including fentanyl, sufentanil, buprenorphine and analgesic combinations, anesthetics, anorexics, antiarthritics, antiasthmatic agents such as terbutaline, anticonvulsants, antidepressants, antidiabetic agents, antidiarrheals, antihistamines, anti-inflammatory agents, antimigraine preparations, antimotion sickness preparations such as scopolamine and ondansetron, antinauseants, antineoplastics, antiparkinsonism drugs, antipruritics, antipsychotics, antipyretics, antispasmodics, including gastrointestinal and urinary anticholinergics, sympathomimetrics, xanthine derivatives, cardiovascular preparations including calcium channel blockers such as nifedipine, beta-blockers, beta-agonists such as dobutamine and ritodrine, antiarrythmics, antihypertensives such as atenolol, ACE inhibitors such as rinitidine, diuretics, vasodilators, including general, coronary, peripheral and cerebral, central nervous system stimulants, cough and cold preparations, decongestants, diagnostics, hormones such as parathyroid hormone, hypnotics, immunosuppressives, muscle relaxants, parasympatholytics, parasympathomimetrics, prostaglandins, proteins, peptides, psychostimulants, sedatives and tranquilizers.

The invention is also useful in the controlled delivery of peptides, polypeptides, proteins and other macromolecules. These macromolecular substances typically have a molecular weight of at least about 300 daltons, and more typically have a molecular weight of at least about 300 to 40,000 daltons. Specific examples of peptides and proteins in this size range include, without limitation, LHRH, LHRH analogs such as buserelin, gonadorelin, napharelin and leuprolide, GHRH, GHRF, insulin, insulotropin, heparin, calcitonin, octreotide, endorphin, TRH, NT-36 (chemical name: N-[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteoids, $\alpha$ANF, growth factors such as growth factor releasing factor (GFRF), $\beta$MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-1, interleukin-2, menotropins (urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, bradykinin antagonists, CD4, ceredase, CSl's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant), and TGF-beta.

Additional agents include pilocarpine nitrate, lidocaine hydrochloride, hydrocortisone derivatives, sodium salicylate, acetic acid, fluoride anion, lithium, antibiotics such as penicillin and cephalosporin and dexamethasone sodium phosphate, hydromorphone, diazepam salts, antihypertensive agents, bronchodilator agents, peptide hormone and regulatory agents and proteins.

The electrode elements formed using these ionic substances are generally used as the active electrodes, although it would be possible to use them also for the counter electrodes in certain circumstances.

It is also known that iontophoretic delivery devices can be used to deliver an uncharged drug or agent into the body. This is accomplished by a process called electroosmosis. The present invention contemplates this mode of delivery as well. Electroosmosis is the transdermal flux of a liquid solvent (e.g., the liquid solvent containing the uncharged drug or agent) which is induced by the presence of an electric field imposed across the skin by the donor electrode. As used herein, the terms "iontophoresis" and "iontophoretic" refer to (1) the delivery of charged drugs or agents by electromigration, (2) the delivery of uncharged drugs or agents by the process of electroosmosis, (3) the delivery of charged drugs or agents by the combined processes of electromigration and electroosmosis, and/or (4) the delivery of a mixture of charged and uncharged drugs or agents by the combined processes of electromigration and electroosmosis.

The following examples are illustrative of the processes and materials used to obtain the electrode compositions of the invention.

General Protocol

A preferred iontophoretic device has an adhesive active agent loaded reservoir in which the active agent is stable and the reservoir is sufficiently adhesive to hold the device to the skin without aid of mechanical means (e.g. straps). Additionally, the active agent should be soluble in ionic form in the reservoir and the reservoir should contain a minimum of extraneous ions so as to provide for energy efficient active agent delivery.

Ionomeric hydrogels (hydrated ionic polymers) can be formed from monomeric species by a free-radical polymerization process and can be used as a reservoir. Unfortunately, many active agents are susceptible to degradation under the conditions necessary for free-radical polymerization, thus preventing active agent incorporation prior to polymerization. Additionally, ionomeric hydrogels contain mobile "counter-ions" which serve to counter-balance the charge of the ionomeric components of the hydrogel. If the counter-ion of the hydrogel has the same charge as the active agent ion, (i.e., co-ion), then the counter-ion will carry a portion of the current and the efficiency of drug delivery will be reduced (i.e., co-ion competition).

The examples illustrate embodiments using adhesive ionomeric hydrogels but avoid or minimize drug degradation and co-ion competition. These properties are accomplished by incorporating the active agent into a separate carrier layer that releases active agent to the skin contact layer. Co-ion competition is minimized by selecting the proper form of the active agent and/or proper ionomeric ingredient.

The examples employ an anionic polymeric hydrogel based on the sodium or acid form of acrylamido-methyl-propane-sulfonate (Na-AMPS or H-AMPS) and on a cationic polymeric hydrogel based on methacrylamido-propane-trimethyl-chloride or hydroxide (MAPTAC or MAPTAOH). The examples illustrate the use of these ionomeric polymers in combination with a particular form of the active agent, such as the "free base," "free acid," or "salt" form. The advantages discussed above will be exemplified by combinations of forms of the ionomeric polymer and active agent to create a stable, efficient iontophoretic device.

Other ingredients may be added to the formulation to achieve particular physical or chemical conditions (e.g. conductivity, pH) such as hydrochloric acid or sodium hydroxide, or added to achieve particular ratios of acid to base (i.e. stoichiometry). The addition of other nonionic polymeric ingredients can be made to achieve the desired ratio of ionomeric polymer acid, base or salt to active agent acid, base, or salt. The nonionic polymer components may be present as a copolymer or as a blend (mixture). Examples of nonionic polymers are polyvinyl alcohol (PVA) and hydroxy-ethyl-methacrylate (HEMA). The counter-ion to the ionomeric component (e.g. chloride ion in the case of MAPTAC, or sodium ion in the case of Na-AMPS) can be selected to interact with the electrochemically generated species at the anode or cathode, depending on the active agent charge, in a preferred manner so as to avoid migration of electrochemically generated species into the skin contact layer and/or skin.

EXAMPLE 1

Carrier Layer with Drug Salt

The efficiency of active agent delivery of an iontophoretic device employing an ionomeric hydrogel can be enhanced by selecting an ionomeric species which has the same charge as the active agent to be delivered. If the active agent is a cation then the ionomeric component of the skin contact layer is cationic. If the active agent is an anion then the ionomeric component is anionic. By selecting an ionomer which has the same charge as the active agent ion, the counter-ion to the ionomer will be opposite in charge of the active agent ion and will not compete with the active agent ion for transport. In addition, since the active agent ion and ionomer have the same charge, any tendency of the active agent ion to "associate," "interact," or "bind" to the ionomeric polymeric component will be minimized due to electrostatic repulsion.

In one example, the carrier layer of polyvinyl pyrrolidone, polyvinyl alcohol and glycerol contains the salt hydromorphone hydrochloride (HMHCl). The ionomeric component of the skin contact layer is selected to be a cationic ionomer such as MAPTAC. This ionomer belongs to the class of compounds known as quaternary ammonium salts. To achieve the desired physical properties of the skin contact layer, the MAPTAC is preferably copolymerized or blended with nonionic components such as HEMA or PVA.

When the carrier layer and the skin contact layer come into contact, the hydromorphone hydrochloride migrates into the ionomeric hydrogel of the skin contact layer and forms a loaded hydrogel.

The ionomeric component of the hydrogel is MAPTAC, and has a chloride counter-ion. In a preferred embodiment, the anode contacting the element is silver. Oxidation of silver during iontophoresis would lead to the formation of insoluble silver chloride. This process minimizes migration of silver into the hydrogel and/or skin. The chloride ion in this example can be supplied as the counter-ion of the active agent and/or as the counter-ion of the ionomeric component.

Alternatively, if the active agent salt in the carrier layer, for example sodium salicylate, then the ionomeric component of the skin contact layer would be selected to be anionic, for example Na-AMPS. In this example the hydrogel is in contact with the cathode of the iontophoretic device. The cathode would preferably be composed of a material which upon reduction would absorb sodium ion, for example, sodium tungsten bronze or other intercalation or insertion materials.

EXAMPLE 2

Active Element with Skin contact layer Containing Acidic Excipient and Carrier Layer Containing Active Agent Base Some active agents are available in the "free-base" or "alkaloid" or "base" form. Use of this form of active agent may be commercially practical due to availability, or may be preferred due to free-base stability.

For example, hydromorphone alkaloid which is sparingly soluble in water as the free-base form, can be incorporated in the carrier layer, of polyvinyl pyrrolidone, glycerol and hyroxypropyl cellulose. The skin contact layer would contain an acidic excipient or combination of acidic ingredients (e.g., hydrochloric, sulfuric, nitric, acetic, tartaric, citric and the like). When contact is made between the adhesive and carrier layers, the hydromorphone base, M, is converted to ionic hydromorphone via reaction with the acidic excipient. If hydrogen chloride is used, the reaction, $$M + HCl \rightarrow HM^+ + Cl^-$$

would occur. As a result, the skin contact layer becomes "loaded" with hydromorphone cation and chloride counter-ion. Preferably the acid content of the first layer would be sufficient to convert all active agent base in the carrier layer to the ionic form. In this example, use of a silver anode would result in the formation of silver chloride due to the presence of the chloride counter-ion.

Preferably the ionomeric component of the skin contact layer would be cationic (e.g., MAPTAC). It would have a anionic counter-ion (e.g., $Cl^-$) which will not compete with the hydromorphone cation during iontophoresis.

EXAMPLE 3

Active Reservoir with First Hydrogel Layer Containing Acidic Polymeric Component and Second Layer Containing Active Agent Base This example achieves the same advantages as Example 2, but by use of an acidic polymer rather than the combination of an acidic excipient and cationic polymer as in Example 2. The carrier layer of polyvinyl alcohol and hydroxymethyl cellulose contains hydromorphone alkaloid and the first hydrogel layer contains the acidic polymer, H-AMPS. Preferably the acid content of the first layer is sufficient to convert all of the alkaloid to salt in the carrier layer, but not in great excess.

When contact is established between the adhesive and carrier layers, the alkaloid reacts with the H-AMPS to form the hydromorphone cation:

$$M + HAMPS \rightarrow HM^+ + AMPS^-$$

The addition of chloride to this reservoir can be accomplished by either of two methods. First, an acidic excipient such as HCl can be added to the skin contact layer. The total hydronium ion content of the skin contact layer, as supplied by the acidic excipient and the acidic polymer would preferably be sufficient to convert all alkaloid, but not in great excess.

Second, chloride can be added in the form of hydromorphone hydrochloride in the carrier layer. The ratio of hydromorphone hydrochloride to hydromorphone alkaloid in the carrier layer is determined by the hydronium ion content of the skin contact layer. A combination of these methods can be employed to achieve the desired chloride content. The chloride content is determined by the current density and duration of iontophoresis.

The total amount of hydromorphone in the active element is determined by the therapeutic dose rate and duration of use of the iontophoretic device. To achieve the proper acid content of the skin contact layer and the appropriate total active agent content of the element overall (i.e., little or no excess active agent), or to achieve other preferred physical properties (e.g., flexibility, tackiness, shear strength, etc.) nonionic polymers can be added to the skin contact layer.

For example, the adhesive hydrogel layer may contain H-AMPS blended with PVA, or H-AMPS copolymerized with HEMA. The ratio of acidic polymer to nonionic polymer is determined, by the amount of alkaloid in the carrier layer and by the acid content of the skin contact layer needed for conversion of the alkaloid to drug cation.

Another preferred adhesive composition would be an acidic polymer (e.g., H-AMPS) and a cationic polymer (e.g., MAPTAC), either blended or copolymerized to form a suitable hydrogel. This composition is "amphoteric" since both anionic and cationic polymers are present in the hydrogel. The ratio of acidic polymer to cationic polymer is determined by the amount of alkaloid in the carrier layer and by the amount of chloride required to minimize silver migration.

When contact between a hydromorphone alkaloid loaded carrier layer and H-AMPS/MAPTAC amphoteric skin contact layer is made, the alkaloid is converted to drug cation by chemical reaction.

In general, conversion of an alkaloid or free-base drug in the carrier layer to a drug cation is accomplished by an acid-containing skin contact layer. The acid content of the skin contact layer can be provided by acidic excipients and/or acidic-polymer alone or in combination with nonionic polymers and/or cationic polymers as described above, provided that (1) conversion of alkaloid to drug cation is achieved;
(2) co-ion competition is minimized; and
(3) preferably that an appropriate counter-ion is present considering the nature of the electrochemical reaction at the anode (e.g., chloride for a silver anode).

EXAMPLE 4

Active Element with Skin contact layer Containing Basic Polymeric Component and Carrier Layer Containing Acid Form of the Agent The principles and methods for preparing the element in Example 3 are applicable in this example. The active agent is in "free acid" form and the skin contact layer contains a basic ingredient to convert the free acid to active agent anion upon contact between the adhesive and carrier layers. The carrier layer of polyvinyl alcohol and hydroxymethyl cellulose is formulated to contain salicylic acid and the skin contact layer contains the anionic polymer Na-AMPS and sufficient basic excipient (e.g., NaOH) to convert the salicylic acid to salicylate anion. The cathode in contact with the active element can be sodium tungsten bronze, which will absorb sodium ions during iontophoresis.

Alternatively, the skin contact layer could contain sufficient basic polymer, MAPTAOH, to convert the salicylic acid to anion, or a combination of MAPTAOH and NaOH. To adjust the hydroxide concentration of the skin contact layer and/or to improve the physical properties of the hydrogel, nonionic polymers such as PVA and HEMA could be blended or copolymerized with the ionomeric components.

Alternatively or additionally, an amphoteric hydrogel could comprise the skin contact layer. For example, MAPTAOH and Na-AMPS could be blended or copolymerized in a proportion required to convert salicylic acid to salicylate anion.

In general, the skin contact layer should contain basic excipients and/or basic polymers in combination with nonionic and/or anionic polymers, provided that, (1) conversion of drug free acid to drug anion is achieved,
(2) co-ion (anionic) competition is minimized, and (3) that an appropriate counter-ion is present in sufficient quantity to satisfy the preferred electrochemical reaction at the cathode (e.g., insertion of sodium ion into sodium tungsten bronze).

EXAMPLE 5

About 10 grams of lidocaine hydrochloride are dissolved in 270 ml of deionized water in a 1 liter flask. To that solution about 300 grams of glycerine followed by about 300 grams of propoxymethyl cellulose are added. Next, a previously mixed combination of 225 grams of gelatin and 37.5 grams of polyvinyl alcohol is added. The resulting layers of components is stirred until the mixture is difficult to stir. The mixture is heated to a temperature of approximately 75° C. to become a fluid mix of carrier layer and lidocaine hydrochloride.

At the same time, a combination of 2-acrylamido-2-methylpropane sulfonic acid and methylene bis-acrylamide cross-linker are polymerized by aqueous medium free-radical cross-linking techniques in an electrode element insert mold. Plasticizer is also added at about 50% completion of reaction by stirring into the reaction mixture. The mixture is allowed to cure to form the skin contact layer.

The fluid mix of carrier layer and lidocaine hydrochloride is poured into the mold on top of the skin contact layer. Optionally a polyethylene membrane coated with silicone as a release agent is laid down on the surface of the skin contact layer to form the impervious barrier. The fluid carrier layer is allowed to resolidify to form the active two layer element.

The various components, including the skin contact layer polymer, carrier layer polymer and the active agent given in the foregoing procedure, and any other components which may be used, are preferably provided in such relative amounts as to form a flexible, self-supporting element with substantial shape retention, which is adhesive and which is electrically conductive. The components may be adjusted to form a composition of other physical consistency, as discussed above, if desired.

In terms of the percentage of weight of the total adhesive composition it has been found that 20 to 50% variations in the weight percentages of the foregoing components given in the examples provides electrodes of desirable adhesiveness and physical consistency.

The composition with antiarrhythmic agent propranolol may be used in a method for treatment of irregular heart beat. In this method, the element carrying the pharmaceutical agent is applied to the body, and electrical current is generated through the mixture to transport the agent into the body. The invention permits precise control of the agent introduced into the body. At the same time it substantially simplifies the medical procedures necessary to introduce the agent, thus making it much more practical to use as a means of treating large numbers of persons. The more controlled and easier application also results in the iontophoretic method being much more practical with the other active agents listed above. It will be appreciated that the same advantage, and other advantages may be obtained with any active agents for which the iontophoretic process has been shown, or will be shown to be applicable.

While the invention has been described above in connection with the particular embodiments and examples, one skilled in the art will appreciate that the invention is not necessarily so limited and that numerous other embodiments, examples, uses and modifications of an departures from the embodiments, examples and uses may be made without departing from the inventive concepts.

What is claimed is:

1. A device suitable for iontophoretic administration of an active agent through a body surface of a host, comprising:

a source of current;

an active electrode element in electrical contact with the source of current and adapted to make ion-transmitting contact with the body surface, the active electrode element comprising an ionomeric layer and an overlapping carrier layer, the ionomeric layer adapted to be placed in ion-transmitting relation with the body surface, and the carrier layer being compatible with and containing the active agent in a freely mobile form, means for maintaining the carrier layer separate from the ionomeric layer so as to prevent transport of the active agent into the ionomeric layer, means enabling the carrier layer to be placed into contact with the ionomeric layer to permit transport of the active agent into the ionomeric layer; and a counter electrode element in electrical contact with the current source and adapted to be placed in ion-transmitting relation with the body surface.

2. A device according to claim 1 wherein the ionomeric layer comprises an ionic organic polymer having at least some pendent substituents capable of being ionic.

3. A device according to claim 2 wherein the ionomeric layer is adhesive.

4. A device according to claim 2 wherein the ionomeric layer further comprises ingredients selected from the group consisting of a tackifier, a neutral polymer, surfactant, an ionizing reagent, a plasticizer, and any combination thereof.

5. A device according to claim 2 wherein the ionomeric layer contains a substance selected from the group consisting of an acid and a base, and the ionic organic polymer is amphoteric.

6. A device according to claim 2 wherein the ionic organic polymer is from about 1% to about 100% by weight of the polymers in the ionomeric layer.

7. A device according to claim 2 wherein the ionic organic polymer has a mobile counter ion, the active agent is ionized and the charge of the mobile counter ion is opposite the charge of the ionized active agent.

8. A device according to claim 1 wherein said means for maintaining includes an impervious barrier between the ionomeric and carrier layers, the barrier being capable of being breached.

9. A device according to claim 8 wherein said means enabling the carrier layer to be placed into contact with the ionomeric layer includes a piercing plunger positioned in piercing relation with the impervious barrier so as to perforate the impervious barrier and permit transport of said active agent between the carrier and ionomeric layers.

10. A device according to claim 8 wherein the barrier is removable.

11. A device according to claim 8 wherein the carrier layer is selected from the group consisting of a liquid, viscous fluid and powder and the barrier is selected from the group consisting of a pouch, bag, a membrane and a combination of a housing for the active electrode element and a membrane disposed within the housing.

12. A device suitable for iontophoretic administration of an active agent through the body surface of a host, comprising:

a source of current;

an active electrode element in electrical contact with the source of current and adapted to make ion-transmitting contact with the body surface, the active electrode element comprising a ionomeric layer and an overlapping carrier layer, the ionomeric layer being adapted to be placed in ion-transmitting relation with the body surface, and being comprised of an ionic organic polymer having at least some pendent substituents with the same charge as the charge of the active agent in an ionized form, and the carrier layer being compatible with and containing the active agent in a freely mobile form, means enabling transport of the active agent from the carrier layer to the ionomeric layer; and a counter electrode element in electrical contact with the current source and being adapted to be placed in ion-transmitting relation with the body surface.

13. A device according to claim 2 or 12 wherein the ionic organic polymer comprises a substance having a backbone selected from the group consisting of a polyolefin, polycarbonate, polyester, polyether, polyurethane and polyepoxide backbone, with said pendent substituents selected from the group consisting of (alkyl, aryl or aralkyl) carboxylic, phosphoric, glycolic or sulfonic acid and (alkyl, aryl or aralkyl) amine or ammonium, wherein the backbones form a state selected from the group consisting of hydrous-gelled and cross-linked, and any physical combination of said backbones and substituents.

14. A device according to claim 1 or 12 wherein the carrier layer comprises a substance selected from the group consisting of an organic polymer having polar pendent substituents and a polar natural material and a semi-synthetic material.

15. A device according to claim 14 wherein the carrier layer substance is the organic polymer and is selected from the group consisting of a cellulosic derivative, an alginate derivative, a starch derivative, a dextran, a polysaccharide, a hydrogel polymer having a backbone selected from the group consisting of a hydrous-gelled, linear polyolefin, polycarbonate, polyester, polyether, polyurethane and polyepoxide backbone, with backbone substituents selected from the group consisting of (alkyl, aryl or aralkyl) alcohol, amide, ketone, nitrogen heterocycle or ester pendent substituents, and any combination thereof.

16. A device according to claim 1 or 12 wherein the carrier layer is in a form selected from the group consisting of a gel, solid, hydrogel, powder, liquid and viscous fluid.

17. A device according to claim 12 wherein said means for enabling transport includes an impervious barrier between the ionomeric and carrier layers, the barrier being capable of being breached.

18. A device according to claim 17, wherein said means enabling transport of the active agent from the carrier layer to the ionomeric layer includes a piercing plunger positioned in piercing relation with the impervious barrier so as to perforate the impervious barrier and permit transport of said active agent between the carrier and ionomeric layers.

19. An active electrode element for an iontophoretic device suitable for administration of an active agent through a body surface of a host, comprising an ionomeric layer and an overlapping carrier layer, the carrier layer being compatible with and containing the active agent in a freely mobile form, means for maintaining the carrier layer separate from the ionomeric layer so as to prevent transport of the active agent into the ionomeric layer, means enabling the carrier layer to be placed into contact with the ionomeric layer to permit transport of the active agent into the ionomeric layer.

20. An element according to claim 19 wherein the ionomeric layer comprises a polymer selected from the group consisting of a gelled, hydrated, ionic organic polymer having pendent substituents capable of being ionic and a cross-linked, hydrated, ionic organic polymer having pendent substituents capable of being ionic.

21. An element according to claim 20 wherein the ionomeric layer further comprises ingredients selected from the group consisting of a tackifier, a neutral polymer, a surfactant, an ionizing reagent, a plasticizer, and any combination thereof.

22. An element according to claim 20 wherein the ionomeric layer contains a substance selected from the group consisting of an acid and a base, and the ionic organic polymer is amphoteric.

23. An element according to claim 20 wherein the ionomeric layer contains an ionic organic polymer component which comprises a substance having a backbone selected from the group consisting of a polyolefin, polycarbonate, polyester, polyether, polyurethane and polyepoxide backbone with pendent substituents selected from the group consisting of (alkyl, aryl or aralkyl) carboxylic phosphoric, glycolic or sulfonic acid pendent substituents and (alkyl, aryl or aralkyl) amine or ammonium pendent substituents wherein the backbones form a state selected from the group consisting of hydrous-gelled and cross-linked, and any physical combination of said backbones and substituents.

24. An element according to claim 20 wherein the ionic organic polymer is from about 1% to about 100% by weight of the polymers present.

25. An element according to claim 20 wherein the ionic organic polymer has a mobile counter ion, the active agent is ionized and the charge of the mobile counter ion is opposite the charge of the ionized active agent.

26. An element according to claim 19 wherein the carrier layer comprises a substance selected from the group consisting of an organic polymer having polar pendent substituents, a polar natural material and a semi-synthetic material.

27. An element according to claim 26 wherein the carrier layer substance is the organic polymer and is selected from the group consisting of a cellulosic derivative, an alginate derivative, a starch derivative, a dextran, a polysaccharide, a hydrous-gelled linear organic polymer having a backbone selected from the group consisting of polyolefin, polycarbonate, polyester, polyether, polyurethane or polyepoxide backbone with backbone substituents selected from the group consisting of (alkyl, aryl or aralkyl) alcohol, amide, ketone or ester pendent substituents, and any combination thereof.

28. An element according to claim 19 wherein the carrier layer is a hydrogel that is substantially dehydrated.

29. An element according to claim 19 wherein the carrier layer is selected from the group consisting of powder, solid, gel, hydrogel, liquid and viscous fluid.

30. An element according to claim 19 wherein the means for maintaining the carrier layer separate from the ionomeric layer includes an impervious barrier between the ionomeric and carrier layers, the barrier being capable of being breached.

31. An element according to claim 19 wherein the ionomeric layer comprises an ionic organic polymer having at least some pendent groups with the same charge as the charge of the active agent in an ionized form.

32. A method for iontophoretically administering an active agent through a body surface of a host comprising:
applying to the body surface active and counter electrode elements, the active electrode element comprising an ionomeric layer and an overlapping carrier layer, the ionomeric layer being arranged to be placed in ion-transmitting relation with the body surface and the carrier layer being compatible with and containing the active agent in a freely mobile form, being separated from the ionomeric layer so as to prevent transport of active agent into the ionomeric layer but being capable of being placed into contact with the ionomeric layer to permit transport of active agent into the ionomeric layer;
contacting the ionomeric layer and the carrier layer; and
generating an electric potential between the active and counter electrode elements and across the body surface such that the active agent is transported to the body surface.

33. A method according to claim 32 wherein the counter electrode element is displaced a distance on the body surface from the active electrode element and is composed of an adhesive, conducting polymer gel.

34. A method according to claim 32 further comprising the step of activating the ionomeric and carrier layers before the active electrode element is applied to the body surface.

35. A method according to claim 32 wherein an impervious barrier is positioned between the ionomeric and carrier layers and the activating step includes breaching the impervious barrier.

36. A method according to claim 32 wherein the ionomeric layer contains water, an amphoteric organic polymer and a substance selected from the group consisting of an acid and a base, and the carrier layer is a dehydrated material which is hydrated before, during or after the applying step.

37. A method according to claim 32 further comprising providing a silver material as part of the active electrode element, contacting at least a portion of the active electrode element with the silver material and connecting the generated electric potential to the active electrode element through the silver material.

38. A method according to claim 32 wherein the ionomeric layer is an ionizable organic polymer having a mobile counter ion, the active agent is ionized and the charge of the mobile counter ion is opposite the charge of the ionized active agent.

39. A method for iontophoretically administering an active agent through a body surface of a host comprising:
applying to the body surface a single layer active electrode element and a counter electrode element, the active electrode element being arranged to be placed in ion-transmitting relation with the body surface, the active electrode element comprising ionized active agent and an ionic organic polymer component having at least some pendent groups with the same charge as the ionized active agent;
generating an electric potential between the active and counter electrode elements and across the body surface such that the active agent is transported to the body surface; and
using the ionic organic polymer component to at least in part maintain the conductivity of the active electrode element during the transport of the active agent to the body surface.

40. A method according to claim 39 further comprising hydrating a single, substantially dry polymer element with an aqueous medium to produce the single layer active electrode element containing the active agent.

41. A method according to claim 40 wherein the single substantially dry polymer element contains the active ingredient prior to hydrating with the aqueous medium.

42. A method according to claim 40 wherein the aqueous medium contains the active agent.

43. A method according to claim 39 wherein the single layer element contains water, an amphoteric organic polymer as the ionic polymer component, and a substance selected from the group consisting of an acid and a base.

44. A method according to claim 39 further comprising providing a silver material as part of the active electrode element, contacting the single layer with the silver material, and connecting the generated electric potential to the active electrode element through the silver material.

* * * * *